United States Patent [19]
Seager et al.

[11] Patent Number: 5,967,373
[45] Date of Patent: Oct. 19, 1999

[54] PRODUCT DISPENSER HAVING SEPARABLE REFILL CARTRIDGE AND STAGING AND LOCKING STRUCTURE

[75] Inventors: Richard H. Seager, Mystic, Conn.; Peter Piscopo, Medford; Alfred J. Astoreca, Annandale, both of N.J.

[73] Assignee: The Plastek Group, Erie, Pa.

[21] Appl. No.: 09/073,732

[22] Filed: May 6, 1998

Related U.S. Application Data

[63] Continuation-in-part of application No. 08/903,831, Jul. 31, 1997, Pat. No. 5,881,921, which is a continuation-in-part of application No. 08/851,770, May 6, 1997, Pat. No. 5,881,920.

[51] Int. Cl.⁶ ........................................................ B67D 5/52
[52] U.S. Cl. .................. 222/137; 222/153.13; 222/145.3
[58] Field of Search ................................. 222/145.3, 137, 222/153.13, 325, 326, 327, 1

[56] References Cited

U.S. PATENT DOCUMENTS

| | | | |
|---|---|---|---|
| 3,767,085 | 10/1973 | Cannon et al. ..................... | 222/137 X |
| 4,368,830 | 1/1983 | Soughers ........................ | 222/153.13 X |
| 4,598,843 | 7/1986 | Foster et al. ....................... | 222/153.13 |
| 5,289,949 | 3/1994 | Gentile .................................... | 222/137 |
| 5,335,827 | 8/1994 | Gentile .................................... | 222/137 |

*Primary Examiner*—Gregory L. Huson
*Attorney, Agent, or Firm*—Bachman & LaPointe, P.C.

[57] ABSTRACT

A product dispenser includes a cartridge containing a product; a housing having a base member and a cartridge receiving member movably mounted to the base member between a shipping position wherein the cartridge receiving member is substantially extended from the base member, and a use position wherein the cartridge receiving member is at least partially retracted relative to the base member from the shipping position, the cartridge receiving member having a sidewall defining an interior space for receiving the cartridge; an access defined by the sidewall for installing and removing the cartridge in the interior space; structure associated with the housing for dispensing the product from the cartridge; and structure for resisting dispensing motion of the cartridge receiving member relative to the base member from the shipping position toward the use position.

18 Claims, 8 Drawing Sheets

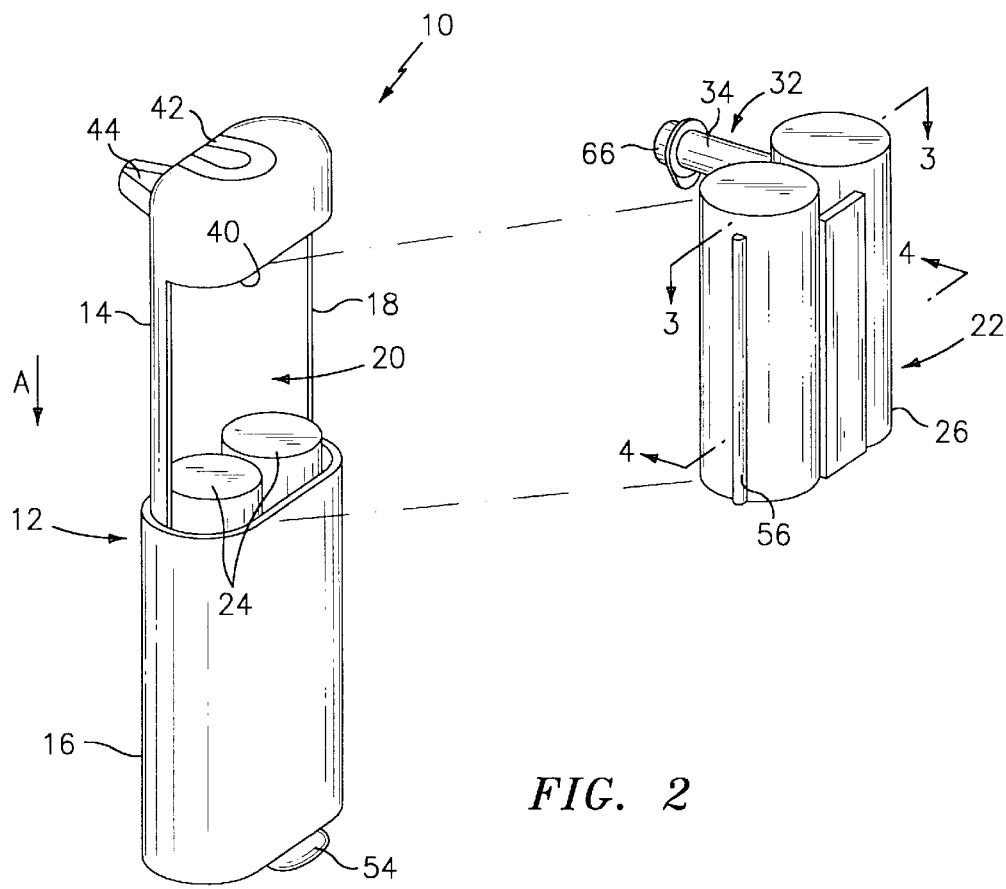
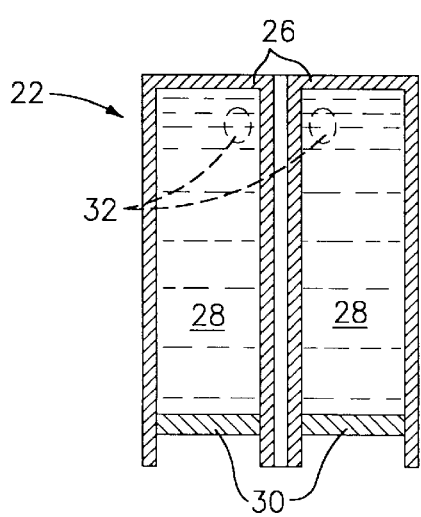
FIG. 4
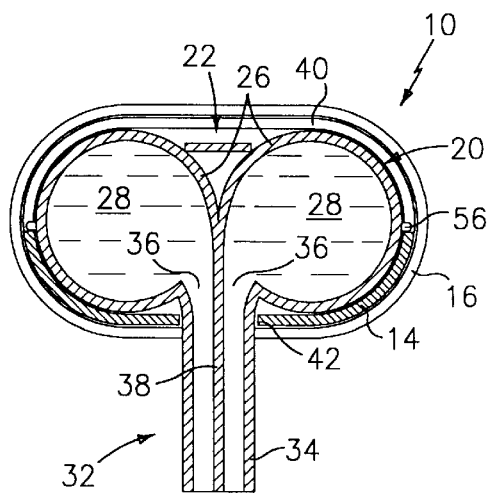
FIG. 3
FIG. 2

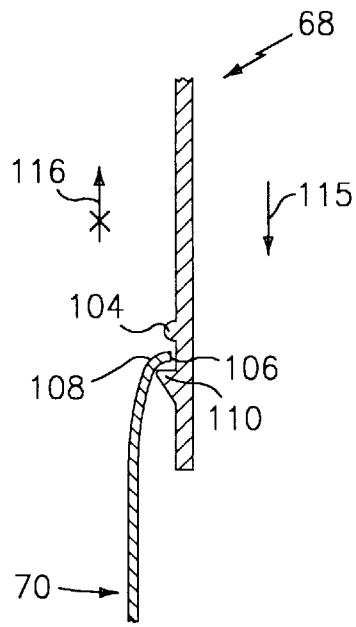 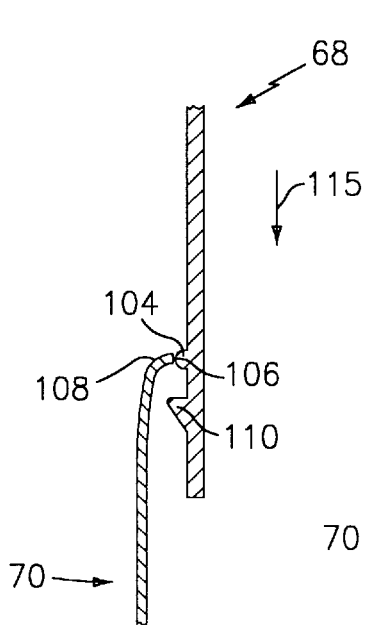 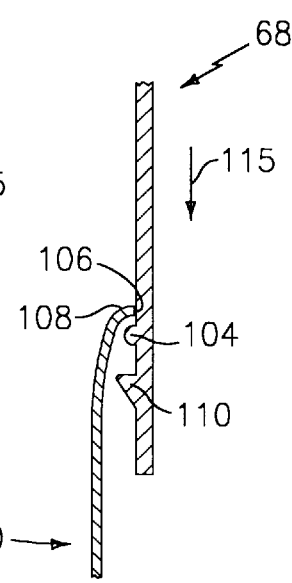
*FIG. 9a*    *FIG. 9b*    *FIG. 9c*
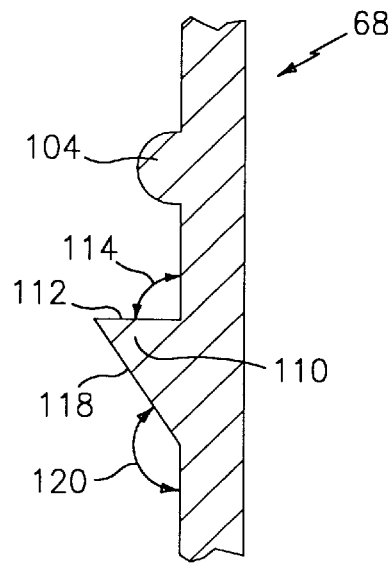 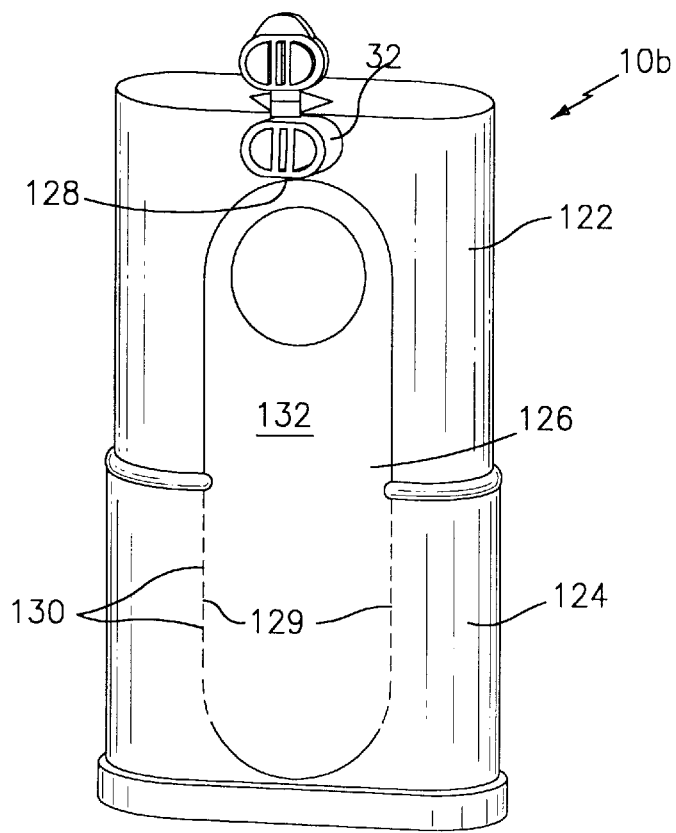
*FIG. 10*    *FIG. 11*

PRODUCT DISPENSER HAVING SEPARABLE REFILL CARTRIDGE AND STAGING AND LOCKING STRUCTURE

CROSS-REFERENCE RELATED APPLICATION

This application is a continuation-in-part of U.S. patent application Ser. No. 08/903,831, filed Jul. 31, 1997 now U.S. Pat. No. 5,881,921, which is a continuation-in-part of U.S. patent application Ser. No. 08/851,770, filed May 6, 1997 now U.S. Pat. No. 5,881,920.

BACKGROUND OF THE INVENTION

The invention relates to a product dispenser and, more specifically, to a dispenser having a separable refill cartridge.

A number of products and containers are on the market in connection with products, specifically dental preparations, wherein a combination of two substances or ingredients are provided. For example, U.S. Pat. No. 4,687,663 is drawn to an article for storage and delivery of baking soda and peroxide preparations. As pointed out in this patent, hydrogen peroxide and sodium bicarbonate may not normally be premixed, as they immediately react and are thereby rendered ineffective for subsequent use. The '663 patent, as well as U.S. Pat. Nos. 4,964,539, D315,496, 5,020,694, 5,038,963 and 5,289,949 are drawn to dispensing containers addressing the problem of keeping sodium bicarbonate and hydrogen peroxide separate until use.

Containers such as those described in U.S. Pat. No. 5,289,949 mentioned above include a base portion and a housing/cartridge structure which slidably moves over the base portion. The product is contained in two cylinders which are an integral portion of the upper housing structure. When product from the cylinders is exhausted, the entire upper portion of the package must be discarded and replaced, leaving only the base as a reusable element.

The container of the above-mentioned U.S. Pat. No. 5,289,949 and others are successful at providing product in a form wherein the hydrogen peroxide and sodium bicarbonate are maintained in separate sections of a container. However, consumers recognize the waste in discarding the entire upper housing/cartridge structure, and the need remains for a solution to this problem.

Frequently, dispensers for dentifrice and the like are shipped in a fully assembled condition so as to eliminate the need for assembly at the destination of the dispenser. However, this can easily lead to dispensers which can be inadvertently compressed or otherwise actuated so as to dispense product, or to pressurize product, during shipping. This is undesirable.

It is therefore the primary object of the present invention to provide a product dispenser having a readily interchangeable refill cartridge wherein the entire housing is reusable.

It is a further object of the present invention to provide a product dispenser wherein removal and installation of replacement cartridges is readily accomplished.

It is a still further object of the present invention to provide a product dispenser having a separable refill cartridge wherein product portions or components are readily provided through a product outlet or nozzle.

It is another object of the present invention to provide a product dispenser having staging and locking structure for resisting inadvertent and undesirable compressing or other motion and dispensing during shipping of the dispenser.

It is still another object of the present invention to provide a product dispenser having a separable refill cartridge and including locking structure for holding the housing together during removal of the cartridge.

Other objects and advantages will appear hereinbelow.

SUMMARY OF THE INVENTION

In accordance with the present invention, the foregoing objects and advantages are readily attained.

According to the invention, a product dispenser is provided, which product dispenser comprises a cartridge containing a product; a housing having a sidewall defining an interior space for receiving said cartridge; access means formed in said sidewall for installing and removing said cartridge in said interior space; and means associated with said housing for dispensing said product from said cartridge.

In further accordance with the invention, a product dispenser is provided which comprises a cartridge containing a product; a housing having a sidewall defining an interior space for removably receiving said cartridge; said cartridge having a wall structure defining a plurality of discrete product spaces, and an outlet communicated with said plurality of product spaces for dispensing said product, said outlet being connected to said cartridge and extending from said housing when said cartridge is in said interior space; and means associated with the housing for dispensing said product from said cartridge through said outlet.

Still further in accordance with the invention, a cartridge for use in a product dispenser in accordance with the invention is provided, which cartridge comprises a cartridge wall structure defining a plurality of discrete product spaces each containing product; an outlet extending from said cartridge and communicated with each of said plurality of discrete product spaces; and a piston member slidably positioned in each of said plurality of discrete product spaces for driving product from said discrete product spaces out of said outlet.

Also provided in accordance with the invention is a product dispenser which comprises a cartridge containing a product; a housing having a base portion and a cartridge receiving portion movably mounted to said base portion, said cartridge receiving portion having a sidewall defining an interior space for receiving said cartridge; access means defined by said sidewall for installing and removing said cartridge in said interior space; and means associated with said housing for dispensing said product from said cartridge.

Further provided in accordance with the invention is a product dispenser which comprises a cartridge containing a product; a housing having a base member and a cartridge receiving member movably mounted to said base member between a shipping position wherein said cartridge receiving member is substantially extended from said base member, and a use position wherein said cartridge receiving member is at least partially retracted into said base member from said shipping position, said cartridge receiving member having a sidewall defining an interior space for receiving said cartridge; access means defined by said sidewall for installing and removing said cartridge in said interior space; means associated with said housing for dispensing said product from said cartridge; and means for resisting dispensing motion of said cartridge receiving member relative to said base member from said shipping position toward said use position.

BRIEF DESCRIPTION OF THE DRAWINGS

A detailed description of the preferred embodiments of the present invention follows, with reference to the attached drawings, wherein:

FIG. 2 is a rear perspective view of a preferred embodiment of the present invention showing a refill cartridge;

FIG. 3 is a sectional view taken along the line 3—3 of FIG. 2;

FIG. 4 is a sectional view taken along the lines 4—4 of FIG. 2;

FIGS. 9a–c further illustrate a portion of the embodiment of FIG. 8 related to staging and locking structure;

FIG. 10 illustrates an exploded portion of the cartridge receiving member of FIG. 8;

FIG. 11 is a perspective view of a further alternative embodiment of the present invention;

DETAILED DESCRIPTION

The invention relates to a product dispenser advantageously having a separable refill cartridge wherein the entire housing is reusable, and only the product cartridge is removed, disposed of, and replaced with a new refill cartridge.

Figure 1:
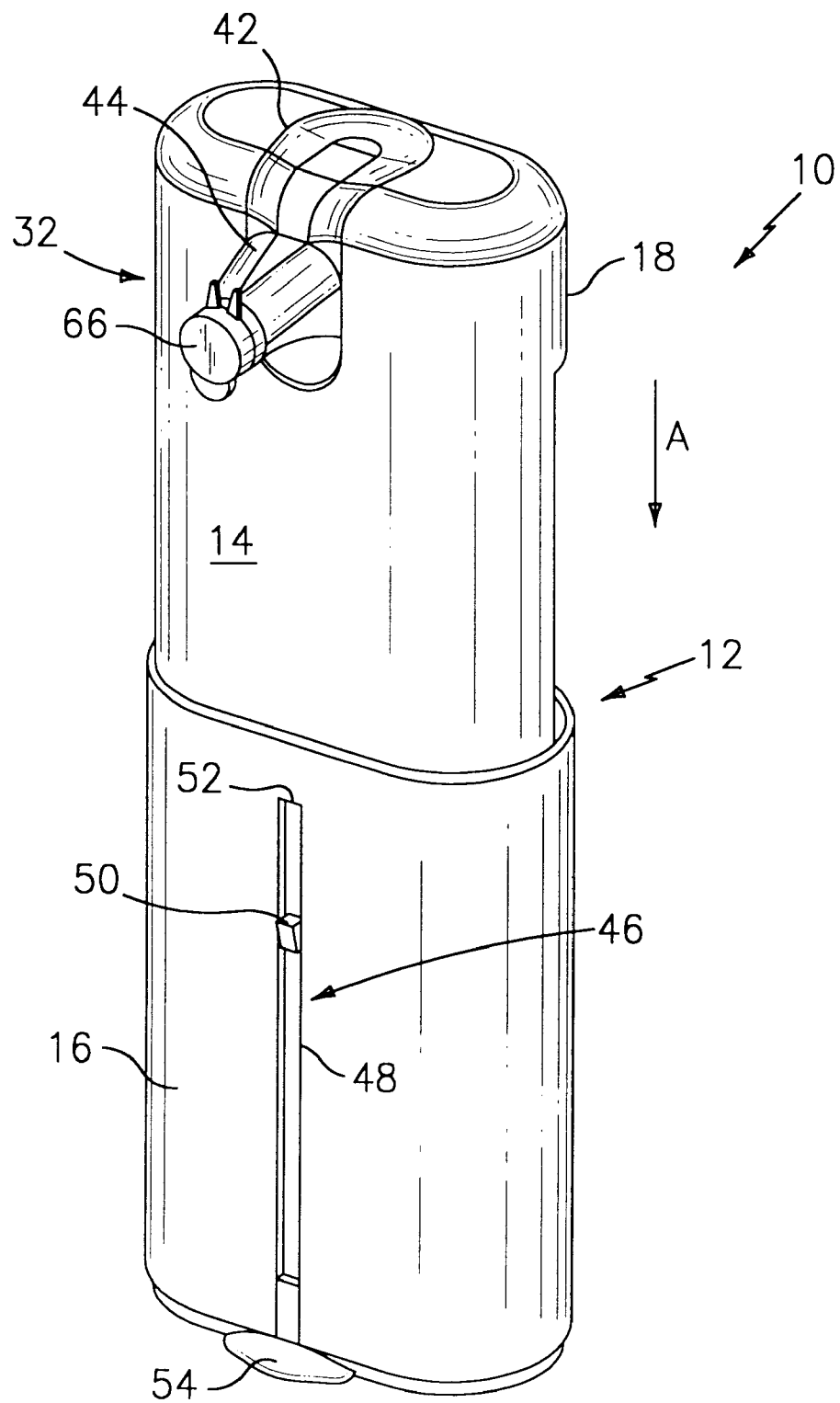
FIG. 1 is a perspective view of a product dispenser in accordance with the present invention.

FIG. 1 shows a perspective view of a product dispenser in accordance with the invention, which will generally be referred to in the drawings by reference numeral 10. According to the invention, dispenser 10 has a housing 12 preferably provided having an upper housing portion 14 and a lower housing portion 16 which are movably mounted together so that upper housing portion 14 can be depressed relative to lower housing portion 16 so as to dispense product as will be further discussed below.

Upper housing portion 14 preferably has a side wall 18 defining an interior space 20 for receiving a cartridge 22, which cartridge 22 contains product to be dispensed. Upper housing portion 14 may have a sidewall 18 in the form of a substantially elongate oval-shaped sleeve, as shown, in this embodiment having a generally closed top and a generally open bottom.

Lower housing portion 16 preferably also includes a side wall or sleeve portion sized to slidably receive upper housing portion 14, for example with upper housing portion 14 within lower housing portion 16 as shown in FIG. 1. Of course, the reverse of this configuration could also be provided. Referring also to FIG. 2, lower housing portion 16 preferably houses a ram structure 24 which interacts with cartridge 22 during depression of upper housing portion 14 relative to lower housing portion 16 so as to dispense product out of cartridge 22 as desired.

Cartridge 22 preferably has a wall structure 26 defining first and second chambers 28 (FIGS. 3, 4) for containing separate portions or components of product to be dispensed therefrom. As shown in FIG. 4, wall structure 26 defines chambers 28 substantially discretely from one another such that a product portion or component in one chamber 28 is not exposed to the product or component in the other chamber 28. This is advantageous for use, for example, in dispensing toothpaste or dentifrice components such as hydrogen peroxide and sodium bicarbonate, which are advantageous when combined but which cannot be mixed until they are to be used. A plunger 30 is preferably provided within each chamber 28 for driving product out of chamber 28 when desired. In this regard, cartridge 22 has an outlet structure 32, preferably in the form of a nozzle 34 communicated with an outlet 36 from each chamber 28. As shown in FIG. 3, suitable divider structure 38 may be provided within nozzle 34 so as to insure that components from chambers 28 are maintained separate and discrete until they are to be used. Structure 38 preferably extends to the end of nozzle 34 as shown.

In the embodiment of FIGS. 1–4, nozzle 34 is preferably provided as an integral portion of or otherwise affixed to cartridge 22 such that each cartridge 22 has a fresh nozzle 34 or outlet structure, thereby avoiding excessive product buildup and the like from extended use of a single nozzle.

Returning to FIG. 2, ram structure 24 is preferably provided and sized sufficiently so as to extend upwardly into chambers 28 and engage plungers 30 so that movement of upper housing portion 14 relative to lower housing portion 16 moves cartridge 22 relative to ram structure 24, thereby upwardly displacing plungers 30 within chambers 28 and dispensing product from outlets 36 as desired.

Still referring to FIG. 2, and as set forth above, upper housing portion 14 preferably includes side wall 18 defining interior space 20 for receiving cartridge 22 as indicated in the drawing. In accordance with this embodiment of the invention, and advantageously, side wall 18 is provided with a cutout 40 for providing access to interior space 20, advantageously while housing portions 14, 16 are assembled together. The removal of a spent cartridge and installation of a new cartridge is thereby readily facilitated by allowing access to interior space 20 through cutout 40 in side wall 18. Cutout 40 allows cartridge 22 to be interchanged without disassembling upper housing portion 14 from lower housing portion 16, thereby simplifying use by a consumer.

Referring back to FIG. 1, upper housing portion 14 is preferably provided with an additional cutout 42 for receiving nozzle 34 of cartridge 22 so as to allow nozzle 34 to extend from housing 12 for ease in use of product dispensed therefrom. As shown, housing 12 may be provided with a shroud structure 44 for at least partially encompassing or enclosing nozzle 34 so as to prevent inadvertent damage to nozzle 34, to enhance the appearance of housing 12, and to firmly hold cartridge 22 within interior space 20 as desired.

Upper housing portion 14 and lower housing portion 16 are preferably slidably mounted together, as set forth above. As shown in FIG. 1, a slot and stop structure 46 may also be provided so as to limit a maximum separation movement of upper housing portion 14 relative to lower housing portion 16. As shown in FIG. 1, a slot 48 may suitably be provided in lower housing portion 16, and a stop 50 positioned at a lower portion of side wall 18 of upper housing portion 14 and slidably disposed within slot 48. Upper end 52 of slot 48 serves to engage stop 50 at a maximum "open" position of upper housing portion 14 relative to lower housing portion 16.

Slot 48 may preferably be provided in lower housing portion 14 as a slot passing through the entire thickness of the side wall of lower housing portion 16 such that stop 50 is visible exterior of housing 12. This advantageously allows stop 50 to serve as a "use-up" indicator to a consumer, thereby indicating when cartridge 22 is nearly exhausted of product.

For additional stability, lower housing portion 16 may advantageously be provided with feet 54 or other base-widening structure so as to provide dispenser 10 with increased stability and reduced tendency to tip over.

It should be noted that dispenser 10 may be provided either already including a cartridge 22, or with cartridges 22 packaged separately. By packaging cartridges 22 separately, housing 12 for dispenser 10 could be packaged and shipped in a completely "closed" position of upper thereby providing a significant savings in package sizing which is not possible with dispensers such as those of U.S. Pat. No. 5,289,949.

To insert a cartridge 22 for use, a consumer would slide upper housing portion 14 relative to lower housing portion 16 toward a completely "open" position, for example as illustrated in FIG. 2, so as to expose cutout 40 and thereby allow access to interior space 20. Cartridge 22 is then readily positioned within interior space 20, with nozzle 34 extending outwardly through cutout 42, and is now fixedly mounted within upper housing portion 14. Downward displacement of upper housing portion 14 relative to lower housing portion 16 as shown by arrow A (FIG. 2) serves to downwardly displace cartridge 22 relative to ram structure 24 of lower housing portion 16, upwardly biasing plungers 30 within chambers 28 to force product portions or components out of outlets 36 and into nozzle 34 of outlet structure 32, typically in a non-mixed side-by-side relationship as desired. Product from within cartridge 22 is used in increments by a consumer until the product supply of cartridge 22 is completely exhausted, at which time cartridge 22 can easily be replaced by upwardly sliding upper housing portion 14 relative to lower housing portion 16 back toward the position of FIG. 2 so as to again expose cutout 40 and allow access to interior space 20 for removal of a spent cartridge 22 and installation of a new cartridge in its place.

It should readily be appreciated that in accordance with the present invention, a significantly reduced portion of the overall dispenser or container is now discarded with each refill, thereby providing the opportunity for supplying the consumer with product at a reduced cost.

Cartridge 22 may advantageously be provided with a ridge structure 56 arranged along at least a portion of the side edges of cartridge 22 as shown.

Ridge structure 56 serves advantageously to provide structure for gripping cartridge 22 thereby facilitating installation and removal of cartridge 22 relative to upper housing portion 14. In this regard, ridges 56 are preferably positioned so as to be exposed through cutout 18 when cartridge 22 is installed within interior space 20.

Figure 5:
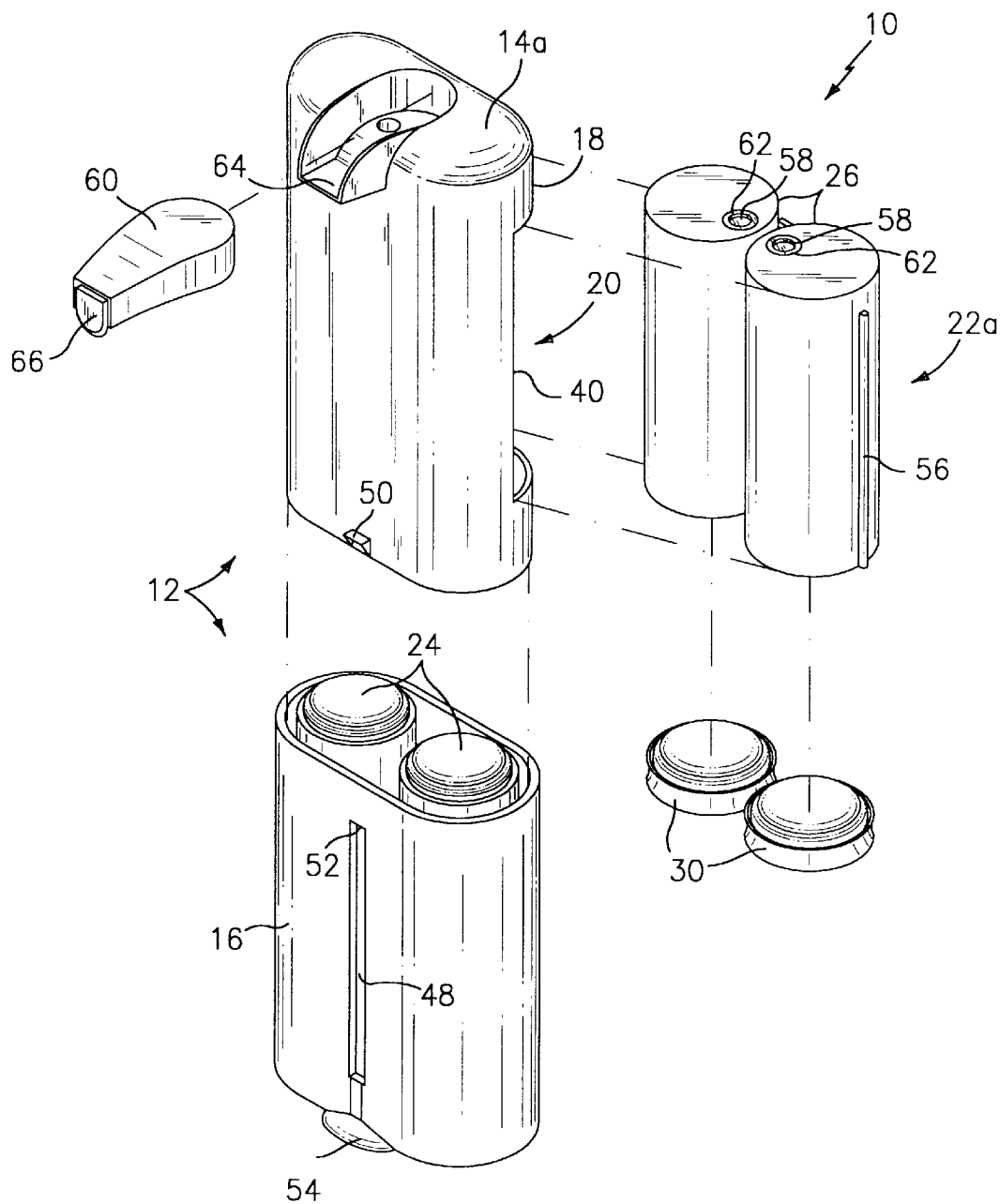
FIG. 5 is an exploded perspective view of an alternative embodiment of the present invention.

Referring now to FIG. 5, an alternative embodiment of the invention is illustrated.

FIG. 5 shows housing 12 having upper housing portion 14a and lower housing portion 16, as well as cartridge 22a for insertion through cutout 40 in interior space 20 as described above. In this embodiment, cartridge 22a is provided having a discrete outlet 56 from each chamber 28, and outlet structure 32 is provided in the form of a nozzle 60 mounted to upper housing portion 14a. In this embodiment, nozzle 60 may be provided with a manifold structure (not shown) for communicating with each chamber outlet 58 and combining same into a single outlet from nozzle 60. In further accordance with this alternative embodiment, each chamber outlet 58 may suitably be provided with a rupturable member 62 covering outlet 58 so as to seal product within chambers 28 until use is desired. Rupturable member 62 may be provided such that an initial use of dispenser 10 exerts sufficient pressure upon rupturable member 62 through product being compressed within chambers 28 by plungers 30 that rupturable member 62 ruptures so as to allow flow or extrusion of product into nozzle 60. Alternatively, a piercing structure (not shown) may be provided at an inlet portion of the manifold structure of nozzle 60 for piercing rupturable members 62 when cartridge 22a is installed within interior space 20.

Still referring to FIG. 5, upper housing portion 14a may suitably be provided with a shelf structure 64 defining a receptacle for nozzle 60 whereby nozzle 60 is advantageously held in place as desired.

The embodiment of FIG. 5 functions in all respects in the same manner as the embodiment discussed above in connection with FIGS. 1–4.

In the above embodiments, both nozzle 34 and nozzle 60 may advantageously be provided with a cap structure 66 for use in closing or sealing the interior portions of nozzle 34, 60 and chambers 28 between uses and/or for storage. Cap structure 66 may suitably be provided as a snap-fit cap for releasably engaging an outlet end of nozzle 34, 60, and may be provided attached to nozzle 34, 60 by a living hinge, or otherwise, or as a separate component.

Figure 6:
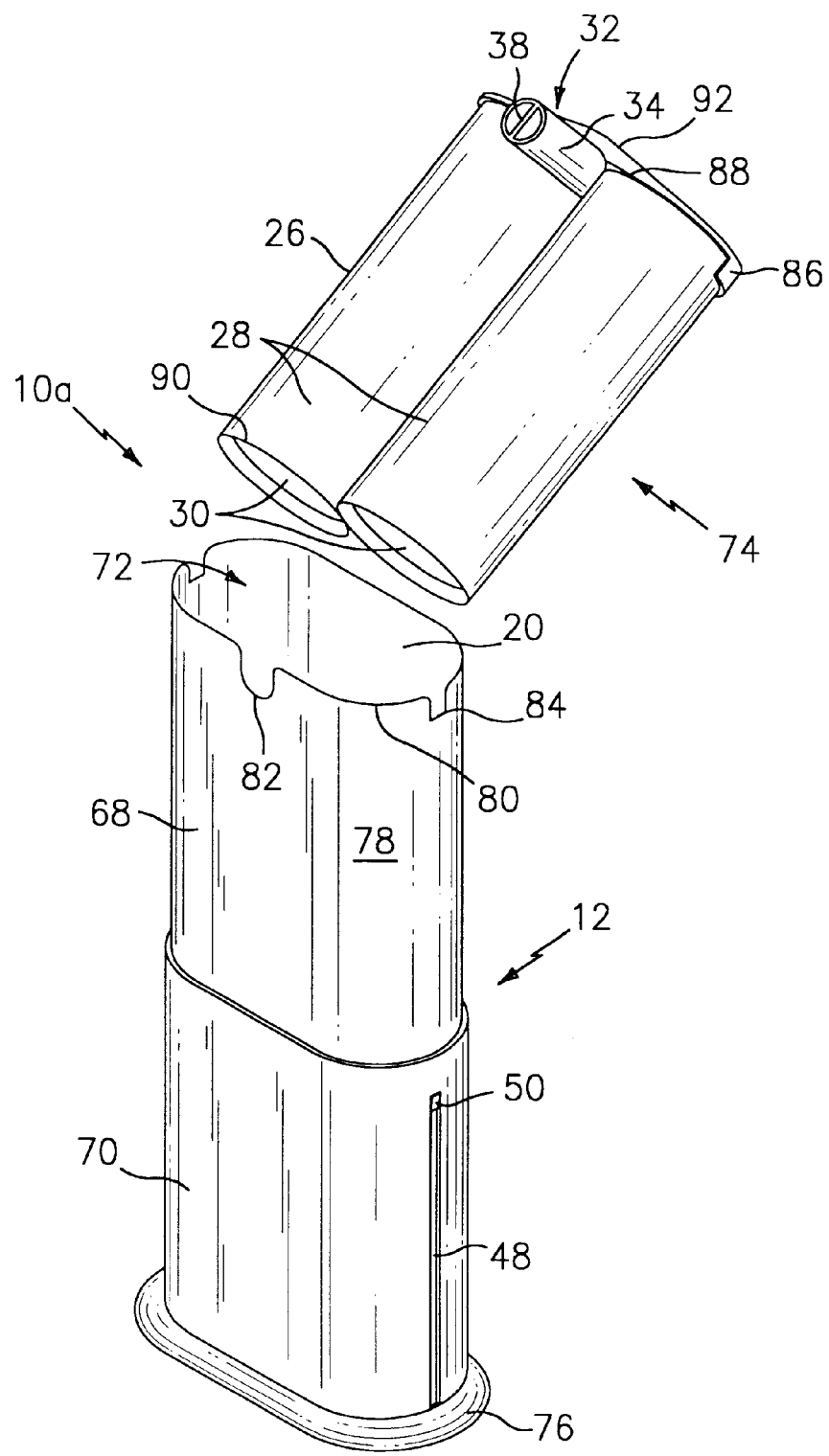
FIG. 6 is a perspective view of a preferred embodiment of a product dispenser according to the invention.
Figure 7:
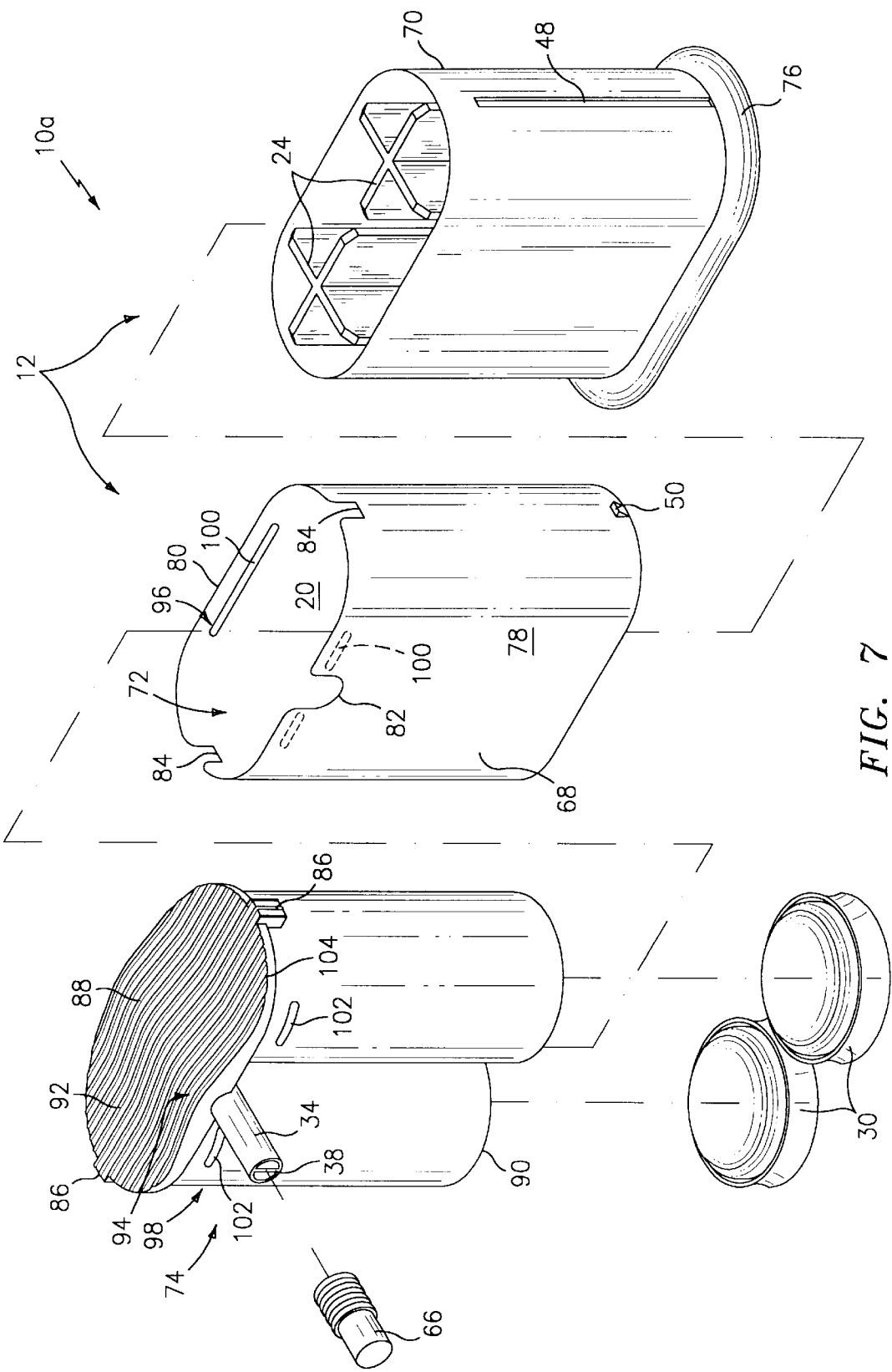
FIG. 7 is an exploded perspective view of the embodiment of FIG. 6.

Referring now to FIGS. 6 and 7, a further preferred embodiment of the present invention is disclosed wherein dispenser 10a includes a housing 12 having an upper housing portion or cartridge receiving portion 68, a lower housing portion or base portion 70, and wherein cartridge receiving portion 68 has a side wall defining a substantially upwardly facing cutout or opening 72 for providing access to interior space 20 whereby cartridge 74 can readily be installed in and removed from interior space 20 of cartridge receiving portion 68 while cartridge receiving portion 68 and base portion 70 are slidably mounted together as shown in FIG. 6. Advantageously, this embodiment provides for "top-loading" of cartridge 74 with respect to housing 12, also as shown in FIG. 6.

Still referring to FIG. 6, base portion 70 is similar to that described in connection with FIGS. 1–5 above, and may further be provided having an extended base 76 for stabilizing same.

As discussed above, cartridge receiving portion 68 is preferably slidably received within base portion 70, and slots 48 in combination with stops 50 may be provided so as to allow slidable engagement of same. Stop 50 serves advantageously in this embodiment to define a maximum open position of cartridge receiving portion 68 relative to base portion 70 from which cartridge 74 can then readily be removed from housing 12. As shown in this embodiment, slot 48 and stop 50 may advantageously be positioned at side locations of housing 12 as opposed to the front location shown in the embodiments of FIGS. 1–5, so as to leave the broad surfaces of housing 12 free for packaging details as desired.

Cartridge receiving portion 68 of housing 12 is also preferably formed of a side wall 78 which defines an upper edge 80 which in turn defines opening 72 for receiving cartridge 74. As shown, edge 80 of cartridge receiving portion 68 is preferably provided having a recess 82 for receiving nozzle 34 of cartridge 74. Further, edge 80 also preferably includes at least one additional recess 84 positioned to receive gripping portions 86 of cartridge 74 which will be discussed below.

Cartridge 74 in accordance with this embodiment of the invention is identical in internal structure to that illustrated in FIGS. 2–4 discussed above. Thus, cartridge 74 includes wall structure 26 defining a plurality of chambers 28 having plungers 30 disposed therein which are upwardly displaced by rams 24 during use of dispenser 10a so as to drive product from each chamber 28 through nozzle 34 of outlet structure 32 for use as desired in accordance with the present invention.

Still referring to FIGS. 6 and 7, cartridge 74 preferably includes, as mentioned above, gripping portions 86 which are preferably arranged at outwardly extending opposed edges or sides of cartridge 74, for example as shown in the drawings, so as to allow convenient grasping of cartridge 74 to remove same from housing 12. As shown, gripping portions 86 may suitably be provided as textured laterally extending regions shaped and positioned to extend through additional recesses 84 of cartridge receiving portion 68.

Cartridge 74 is preferably provided having a top 88, wall structure 26 defining internal chambers 28, and a bottom 90. According to the invention, top 88 is preferably a substantially flat or planar member having a plurality of upwardly extending contoured ridges 92 so as to define a desirable surface for pressing against during use of dispenser 10a. As shown, ridges 92 may suitably be provided having additional thickness at a substantially central area 94 which is preferably substantially laterally aligned with nozzle 34 so as to provide desired structural strength and stability to cartridge 74.

In further accordance with this embodiment of the present invention, structure is also preferably provided so as to allow cartridge 74 to be releasably snapped into place within housing 12.

Referring particularly now to FIG. 7, cartridge 74 and cartridge receiving portion 68 are preferably further provided having interlocking members 96, 98 which serve to releasably engage each other when cartridge 74 is positioned within interior space 20 for use in dispensing product therefrom. Members 96, 98 advantageously serve to hold cartridge 74 in place within housing 12 so as to prevent inadvertent removal of cartridge 74, while preferably being formed so as to have structure providing for disengagement of members 96, 98 before disengagement of slot 48 and stop 50 of cartridge receiving portion 68 and base portion 70 of housing 12. In this manner, advantageously, cartridge 74 can readily be removed from the top of housing 12 while keeping housing 12 in an assembled condition, and a new cartridge 74 can readily be replaced within housing 12 as desired and still within the overall thrust of the present invention wherein a far smaller amount of the overall package of dispenser 10 is disposable.

As shown in FIG. 7, members 96, 98 may suitably be defined as one or more substantially lateral ridges 100 extending inwardly from side wall 78 of cartridge receiving portion 68, and preferably downwardly spaced from edge 80 as shown, while members 98 may suitably be defined as corresponding outwardly extending ridges 102 extending laterally outwardly from wall structure 26 of cartridge 74 and spaced toward bottom 90 from top 88. As shown in FIG. 7, ridges 100, 102 are preferably positioned respectively on cartridge receiving portion 68 and cartridge 74 such that ridges 102 will snap beyond and engage with ridges 100 when cartridge 74 is fully inserted into interior space 20 of cartridge receiving portion 68.

Of course, member 96, 98 could be provided in different numbers than shown in the drawings, and could be provided in any shape desired so as to allow releasable engagement thereof, all within the scope of the present invention.

Still further in accordance with this embodiment of the present invention, top 88 of cartridge 74 preferably further includes a laterally extending flange portion 104 positioned so as to at least partially extend beyond the perimeter of edge 80 of cartridge receiving portion 68 such that, advantageously, when cartridge 74 is inserted within interior space 20, flange portion 104 serves to seat cartridge 74 in a desired position within cartridge receiving portion 68, with ridges 100, 102 engaged to releasably hold cartridge 74 in this position. Flange portion 104 could be an extension from top 88 or could be provided as part of gripping portions 86, or both.

In use, a cartridge 74 is positioned within cartridge receiving portion 68, and exertion of a downward force as shown by arrow A in FIG. 2 causes rams 24 to upwardly displace plungers 30 within chambers 28, thereby dispensing a portion of product from nozzle 34. When cartridge 74 is completely exhausted, cartridge 74 and cartridge receiving portion 68 will have moved together, in fixed relative relation, to a fully depressed position relative to base portion 70. To reload with a fresh cartridge, a consumer would pull upwardly on cartridge 74, for example using gripping portions 86, or on cartridge receiving portion 68 so as to fully extend cartridge receiving portion 68 relative to base portion 70. When stop 50 reaches the upward limit of slot 48, further upward pulling of cartridge 74 relative to housing 12 will disengage ridges 100, 102 so as to allow cartridge 74 to be removed from housing 12 while cartridge receiving portion 68 and base portion 70 are still assembled. By gripping cartridge receiving portion 68, a user can then insert a new cartridge 74 into interior space 20 to the point where ridges 100, 102 re-engage and flange portion 104 rests on edge 80 of side wall 78 of cartridge receiving portion 68. In this position, cartridge 74 is fully installed and dispenser 10a is ready for further use.

Figure 8:
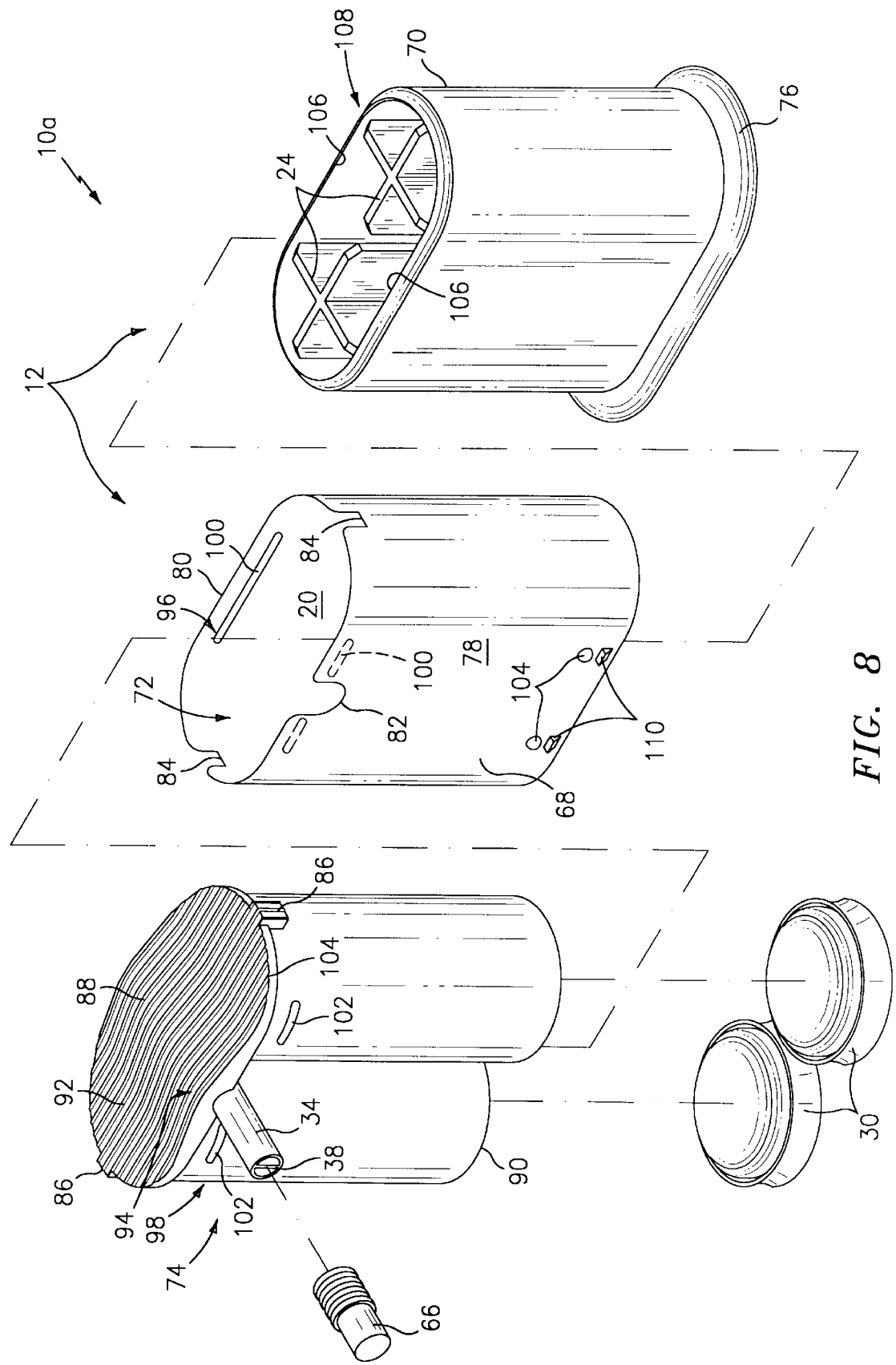
FIG. 8 is an exploded perspective view of a further embodiment of the present invention including staging and locking structure.

Referring now to FIGS. 8–10, a further embodiment of the present invention will be described. As set forth above, it is desirable to provide structure in connection with housing 12 which serves to resist compressing or dispensing movement of cartridge receiving member 14, 68 relative to base member 16, 70. It is particularly desirable to provide structure which resists such motion from a shipping position wherein cartridge receiving member 14, 68 is extended from base member 16, 70 sufficiently to accommodate a full cartridge, toward a use position wherein cartridge receiving member 14, 68 is depressed into or retracted relative to base member 16, 70 so as to dispense product as discussed above. It is also critical that a consumer be able to overcome such resistance or remove the particular structure so as to prepare the dispenser for use. This embodiment is applicable to the structures of the embodiments of FIGS. 1–7, but will be further discussed below in connection with the embodiment of FIGS. 6 and 7 only for the sake of simplicity.

Referring to FIG. 8, this is accomplished by providing one or more staging bumps 104, in this embodiment on an outer periphery of cartridge receiving member 68, and further by providing a lip 106 which in this embodiment is positioned along an upper edge 108 of base member 70. Staging bumps 104 advantageously serve to resist compression movement of cartridge receiving member 68 relative to base member 70 from a shipping position (illustrated in FIG. 9a) toward a use position (illustrated in FIG. 9c).

Staging bumps 104 are preferably substantially smooth or rounded structures which preferably extend substantially perpendicular to a direction of movement (Arrow 115, FIGS. 9a–9c) of cartridge receiving member 68 relative to base member 70 so as to initially resist passage of lip 106 until sufficient force is applied to deflect lip 106 around bump 104 as shown in FIG. 9b. At this point, lip 106 is further smoothly guided over the remainder of staging bump 104 to contact sidewall 78 and smoothly slide along same.

In order to resist depression from the shipping position as desired, it is preferred that staging bumps 104 be positioned vertically on cartridge receiving member 68 so as to substantially coincide with a position wherein cartridge receiving member 68 can receive a full cartridge 74 without rams 24 displacing pistons 20 within cartridge 74. One or more staging bumps 104 may suitably be provided. In the embodiment illustrated, two staging bumps 104 are positioned on a front surface, and two additional staging bumps 104 (not shown) are positioned on a rear surface of cartridge receiving member 68, so as to result in a plurality of staging bumps 104 substantially spaced around cartridge receiving member 68 as desired to provide a stable resistance to depression from the shipping position.

Still referring to FIGS. 8–10, dispenser 10 in accordance with the present invention may also preferably be provided with locking structure for resisting complete separation of cartridge receiving member 68 from base member 70. This is advantageous so as maintain housing 12 as a single element during removal of a spent or empty cartridge. As shown in FIG. 8, locking structure may be provided in the form of one or more teeth 110 preferably positioned so as to engage or lock against lip 106 to prevent further extension or separation movement of cartridge receiving member 68 relative to base member 70. As best illustrated in FIG. 10, teeth 110 are preferably provided having an engaging surface 112 which is positioned at an angle 114 relative to sidewall 78 which is less than or equal to about 90°. In this regard, angle 114 is the angle formed by tooth 110 with cartridge receiving member 68 which faces toward lip 106 when cartridge receiving member 68 is assembled with base member 70. Teeth 110 advantageously serve to engage against separating movement of cartridge receiving member 68 relative to base member 70 as illustrated, for example in FIG. 9a, by the crossed out arrow 116.

Referring back to FIG. 10, teeth 110 may also preferably be provided with a surface 118 facing away from lip 106 when members 68, 70 are assembled, and surface 118 is preferably oriented at an angle 120 with sidewall 78 which is greater than or equal to 90°, preferably at least about 120°, so as to facilitate insertion of cartridge receiving member 68 into base member 70 during initial assembly of housing 12. Surface 118 serves advantageously to guide lip 106 beyond teeth 110 into the shipping position of FIG. 9a as desired.

As with staging bumps 104, teeth 110 may preferably be provided in a plurality, for example having two teeth 110 positioned on a front portion of cartridge receiving member 68, and two teeth (not shown) positioned on a rear portion of cartridge receiving member 68, so as to provide substantially spaced teeth 110 which resist separation of cartridge receiving member 68 from base 70 in a stable fashion.

Teeth 110 and staging bumps 104 are preferably spaced vertically or in the direction of movement of cartridge receiving member 68 relative to base member 70 so as to define a space sufficient to receive lip 106 in the shipping position. This is desirable so as to provide a dispenser 10 for shipping wherein the two portions or members of housing 12 are held in position without undesirable "play" or movement of one member relative to the other.

It should also be noted that although FIGS. 8–10 show staging bumps 104 and teeth 110 on cartridge receiving member 68, and lip 106 on base member 70, these elements could be reversed in location, with a lip positioned on cartridge receiving member 68, and with staging bumps 104 and teeth 110 positioned on base member 70, all within the scope of the present invention. In such a configuration, the lip on cartridge receiving member 68 would most preferably be a radially extending lip, as opposed to the radially inwardly oriented lip 106 of base member 70 of the drawings.

Figures 12, 13:
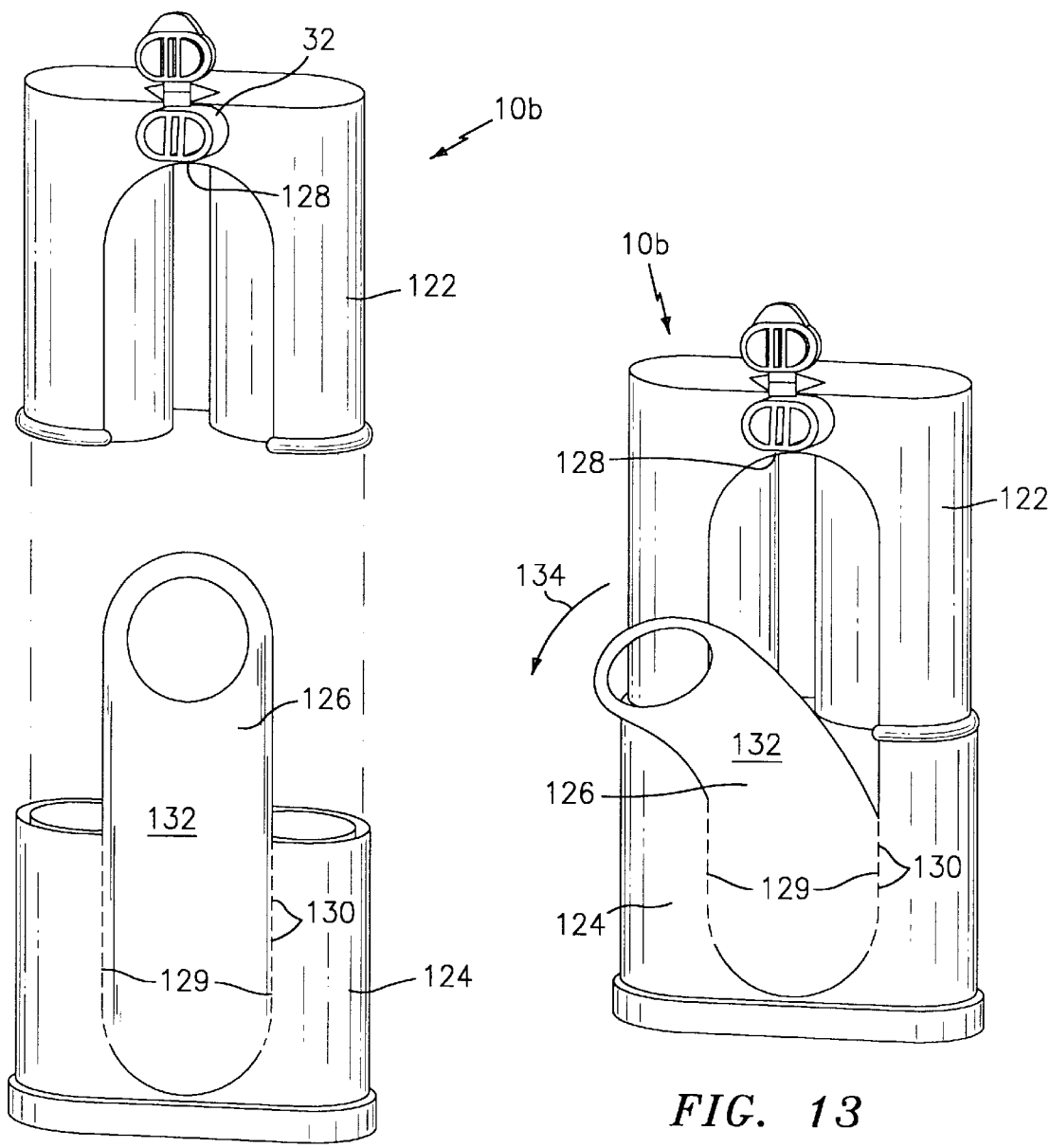
FIG. 12 is an exploded view of the embodiment of FIG. 11.
FIG. 13 is a further perspective view of the embodiment of FIG. 11 showing removal of a staging stop member.

Referring now to FIGS. 11–13, a further alternative embodiment in connection with staging structure is illustrated. In this embodiment, a dispenser 10b is shown having a cartridge receiving member 122 and a base member 124. The internal structure of members 122, 124 could be similar to that described in connection with the embodiments illustrated in FIGS. 1–7, if desired. Alternatively, cartridge receiving member 122 could incorporate as a single member a cartridge containing product to be dispensed as is well known in the art. In this embodiment, a staging stop 126 is preferably provided in the form of a substantially planar member which is removably fixed to base member 124, and abuts against or engages cartridge receiving member 122 so as to prevent dispensing movement of cartridge receiving member 122 relative to base member 124 in a similar manner to the staging bumps discussed above in connection with FIGS. 8–10. Specifically, when staging stop 126 is in position, it abuts against a portion of cartridge receiving member 122, for example against a bottom surface 128 of nozzle member 32, so as to prevent downward displacement of cartridge receiving member 122 relative to base member 124. This advantageously serve to prevent unwanted dispensing or pressurization of product during shipping. When a consumer is ready to use dispenser 10b, staging stop 126 is removed from housing 12, and housing 12 is then free to operate as discussed above to dispense product as desired. In accordance with the embodiment illustrated in FIGS. 11–13, staging stop, 126 is preferably attached to base member 124 along areas or tear lines 129 provided with a series of perforations 130 which serve to allow staging stop 126 to be readily removed from base member 124 for example as illustrated in FIG. 13 (Arrow 134). Of course, scoring and other techniques could also be used in place of or in combination with perforations 130 so as to facilitate removal of stop 126 when desired.

In further accordance with the present invention, staging stop 126 advantageously provides an outwardly facing and readily visible surface 132 which may suitably be employed for displaying advertisement, coupons and the like. A particular advantage of surface 132 is the provision of a readily visible surface to which can be applied coupons or vouchers or the like, for example printed directly on surface 132, and stop 126 could then be removed and redeemed by a consumer in connection with further purchases of the same or different products.

It should be noted that although this disclosure is made in terms of a cartridge having two chambers 28 from which separate product portions or components are dispensed, the teachings of the present invention would be readily applicable to a cartridge having more than two chambers 28, if desired, as well as to a cartridge having chambers 28 of different sizes. This may be suitable, for example, for use in dispensing a product having three or more different components which are to be kept separate, and/or are to be dispensed in different proportions to each other.

Furthermore, although the present disclosure is presented in terms of an extrudable toothpaste product having a sodium carbonate portion and a hydrogen peroxide portion, it should readily be appreciated that the product dispenser of the present invention could readily be applied to dispensing of other products having components which are desired to be kept separate until use.

The various components of dispenser 10 may suitably be provided of injection molded or vacuum formed plastics such as polypropylene, polyethylene and the like. Of course, a number of other alternative materials and manufacturing methods could be used well within the scope of the present invention.

In accordance with the foregoing, it is readily apparent that a product dispenser has been provided having a separable refill cartridge in satisfaction of the above-stated objects of the present invention, and others. This product dispenser advantageously provides for an easily replaceable product cartridge, and a greater percentage of reusable materials in the overall dispenser package.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

We claim:

1. A product dispenser, comprising:
   a cartridge containing a product;
   a housing having a base member and a cartridge receiving member movably mounted to said base member between a shipping position wherein said cartridge receiving member is substantially extended from said base member, and a use position wherein said cartridge receiving member is at least partially retracted relative to said base member from said shipping position, said cartridge receiving member having a sidewall defining an interior space for receiving said cartridge;
   access means defined by said sidewall for installing and removing said cartridge in said interior space;
   means associated with said housing for dispensing said product from said cartridge; and
   means for resisting dispensing motion of said cartridge receiving member relative to said base member from said shipping position toward said use position.

2. A dispenser according to claim 1, wherein said means for resisting motion comprises at least one bump extending from one member of said cartridge receiving member and said base member to engage the other member of said cartridge receiving member and said base member in said shipping position so as to resist said dispensing motion.

3. A dispenser according to claim 2, wherein said base member has an upper edge and wherein said at least one bump extends outwardly from said cartridge receiving member to engage said upper edge when said cartridge receiving member is in said shipping position.

4. A dispenser according to claim 3, wherein said at least one bump comprises a plurality of bumps spaced around said one member.

5. A dispenser according to claim 2, wherein said at least one bump comprises a substantially rounded projection extending substantially laterally from said one member.

6. A dispenser according to claim 2, wherein said cartridge receiving member and said base member have a direction of relative movement, and wherein said at least one bump extends substantially perpendicular to said direction.

7. A dispense according to claim 1, wherein said means for resisting dispensing motion comprises a stop member fixed to one member of said base member and said cartridge receiving member and contacting the other member of said base member and said cartridge receiving member so as to block dispensing motion of said cartridge receiving member relative to said base member from said shipping position toward said use position.

8. A dispenser according to claim 7, wherein said stop member comprises a substantially planar member fixed to said one member substantially parallel to said sidewall of said cartridge receiving member.

9. A dispenser according to claim 8, wherein said substantially planar member includes an outwardly oriented surface whereby indicia can be placed on said stop member in a viewable position.

10. A dispenser according to claim 7, wherein said stop member is connected to said one member along a tear line which is treated to facilitate tearing whereby said stop member is removable to allow motion of said cartridge receiving member relative to said base member from said shipping position toward said use position.

11. A dispenser according to claim 10, wherein said tear line has a series of perforations.

12. A dispenser according to claim 1, further comprising means for slidably locking said cartridge receiving member to said base member.

13. A dispenser according to claim 12, wherein said means for slidably locking comprises at least one tooth arranged on one member of said cartridge receiving member and said base member to engage the other member of said cartridge receiving member and said base member against separation from said shipping position.

14. A dispenser according to claim 13, wherein said at least one tooth member defines an angle with said one member, said angle facing said other member in an assembled position and being less than or equal to about 90°.

15. A dispenser according to claim 14, wherein said at least one tooth member engages against a lip positioned on said other member, and wherein said angle faces said lip in said assembled position.

16. A dispenser according to claim 13, wherein said at least one tooth comprises a plurality of teeth spaced around said one member.

17. A dispenser according to claim 13, wherein said at least one tooth and said at least one bump are mounted on said one member and positioned to define a space therebetween, and wherein said other member has a lip, and wherein said space is sized to receive said lip.

18. A product dispenser, comprising:
   a housing having a base member and a cartridge member containing a product, said cartridge member being movably mounted to said base member between a shipping position wherein said cartridge member is substantially extended from said base member, and a use position wherein said cartridge member is at least partially retracted relative to said base member from said shipping position;
   means associated with said housing for dispensing said product from said cartridge member; and
   means for resisting dispensing motion of said cartridge member relative to said base member from said shipping position toward said use position.

* * * * *